United States Patent [19]

Nishino et al.

[11] 3,957,838

[45] May 18, 1976

[54] PROCESS FOR PRODUCTION OF FATTY ACID SALT AND ESTER THEREOF BY ALKALINE FUSION OXIDATION REACTION

[75] Inventors: Hiroshi Nishino, Tokyo; Hiroshi Maruyama; Masaki Masuda, both of Chiba, all of Japan

[73] Assignee: Kishimoto Sangyo Co., Ltd., Tokyo, Japan

[22] Filed: Sept. 4, 1974

[21] Appl. No.: 503,064

[52] U.S. Cl............................ 260/410.9 R; 260/413; 260/495; 260/531 C
[51] Int. Cl.².......................................... C11C 3/02
[58] Field of Search......... 260/410.9 R, 413, 531 C, 260/495

[56] References Cited

UNITED STATES PATENTS

| | | | |
|---|---|---|---|
| 1,857,921 | 5/1932 | Lazier | 260/495 |
| 2,225,944 | 12/1940 | Sterk | 260/495 |
| 2,824,130 | 2/1958 | Robertson | 260/531 C |
| 2,829,177 | 4/1958 | Cull | 260/495 |
| 3,188,330 | 6/1965 | Heeker | 260/495 |

*Primary Examiner*—Patrick P. Garvin
*Assistant Examiner*—John F. Niebling
*Attorney, Agent, or Firm*—Armstrong, Nikaido & Wegner

[57] ABSTRACT

Fatty acid salts and esters thereof are produced by an alkaline fusion reaction of primary alcohols in the presence of a catalytic amount of zinc or a compound of zinc.

8 Claims, No Drawings

PROCESS FOR PRODUCTION OF FATTY ACID SALT AND ESTER THEREOF BY ALKALINE FUSION OXIDATION REACTION

BACKGROUND OF THE INVENTION

This invention relates to a process for producing fatty acid salts and esters thereof from primary aliphatic alcohols of the structure $RCH_2OH$, where R denotes alkyl, by alkaline fusion in the presence of zinc or zinc compounds.

It is known that primary aliphatic alcohols or aldehydes, upon heating with sodium hydroxide to 260°–300°C., produce sodium salts of corresponding fatty acids as indicated by the following equation:

$$RCH_2OH + NaOH \rightarrow RCOONa + 2H_2$$

It is disclosed in U.S. Pat. No. 2,384,817 that 38% sodium hydroxide solution is used for this reaction by utilizing metal oxides such as cadmium oxide, copper oxide, or nickel oxide as the catalyst. This reaction, however, has been found to be unsuitable for commercial production of certain desirable fatty acid salts.

SUMMARY OF THE INVENTION

According to the present invention, fatty acid salts and esters thereof are produced advantageously on a commercial basis by reacting primary aliphatic alcohols with caustic alkalis at atmospheric pressure employing zinc or zinc compounds such as zinc oxide, zinc chloride, zinc carbonate, or zinc 2-ethylhexaoate as the catalyst.

DETAILED DESCRIPTION OF THE INVENTION

In the process according to the present invention primary aliphatic alcohols having at least 6 and up to 18 carbon atoms, preferably primary aliphatic alcohols having from 6 to 10 carbon atoms, are reacted with caustic alkalis in the presence of zinc or zinc compounds. The alcohol is refluxed during the reaction and water produced in the reaction is distilled out of the reaction system thereby producing the fatty acid salts and esters thereof.

The primary alcohols employed in the process of the invention are those represented by the structural equation $RCH_2OH$ where R is alkyl, such that the primary alcohol has 6 to 18 carbon atoms.

The exact mechanism of the reaction is not completely understood. It is believed, however, that the fatty acid salts and esters thereof are produced through the interaction of the reactions illustrated and discussed below. For convenience the reactions are illustrated employing sodium hydroxide and, as the catalyst, zinc oxide.

The primary alcohol and the caustic alkali in th reaction system react producing water and sodium alcoholate. The water is removed from the system forcing the reaction equilibrium to the right side of the equation (1').

$$RCH_2OH + NaOH \rightleftarrows RCH_2ONa + H_2O \quad (1)$$

The sodium alcoholate converts itself to the aldehyde by the catalysis of the zinc or zinc compound according to the reaction (2).

$$RCH_2ONa \xrightarrow{Zn_0} RCHO + NaH \quad (2)$$

A part of the aldehyde thus formed converts itself to the sodium salt of the fatty acid by the fusion reaction with the sodium hydroxide as indicated in equation (3).

$$RCHO + NaOH \rightarrow RCOONa + H_2 \quad (3)$$

Simultaneously, a portion of the sodium alcoholate formed in the reaction [Equation (1)] catalyzes the condensation of 2 moles of the aldehyde to an ester as shown in Equation (4). (The reaction is the so-called Tischtschenko's reaction.)

$$2RCHO \xrightarrow{RCH_2ONa} RCH_2OOCR \quad (4)$$

Sodium hydride produced in the reaction of equation (2) is converted to the sodium alcoholate by reaction with the alcohol as follows.

$$RCH_2OH + NaH \rightarrow RCH_2ONa + H_2 \quad (5)$$

Although the alcohols which may be used for this invention are the primary aliphatic alcohols having at least 6 and up to 18 carbon atoms, the primary alcohols having from 6 to 10 carbon atoms are preferable because these alcohols have more advantages from the standpoint of practical and economical use.

The caustic alkalis may be used in the form of flake or powder, but the flake form is the best. Sodium hydroxide is generally preferred as the caustic alkali. Hydroxides of other alkali metals, however, may be employed.

Zinc oxide is preferred as the catalyst in the process of the invention but good results are obtained with zinc powder and other zinc compounds including, for example, zinc chloride, zinc carbonate and zinc 2-ethylhexaoate. The catalysts are employed in a catalytic amount which may vary according to the specific reactants. Generally, however, from 0.2 to 3.5% by weight (calculated on the basis of Zn) based on the weight of the alcohol is employed.

The amount of sodium hydroxide employed is preferably from 50 to 90 mol percent based on the amount of alcohol.

To illustrate the practice of the process of the invention the process will be described below for the reaction of 2-ethyl-hexanol with sodium hydroxide in the presence of zinc oxide. The 2-ethyl-hexanol and sodium hydroxide along with the zinc oxide, in definite amounts, are charged to a reactor provided with a reflux condenser. The reaction begins when the temperature reaches the refluxing temperature (182°C.) of the alcohol. As the reaction proceeds the sodium salt of the fatty acid is produced with the generation of hydrogen and water. Additionally, esters and aldehydes are simultaneously produced as by-products to a certain extent. Thus, it may be seen that the alcohol and the caustic alkali react at the refluxing temperature of the alcohol to produce the fatty acid salt effectively. As the reaction proceeds there is caused the production of the ester with an accompanying gradual increase of the temperature of the reaction system. After 90 minutes the temperature rises from the refluxing temperature of the alcohol to 230°C., and the reaction ends. The water formed during the reaction is distilled off. Then, the reaction system is cooled and thereafter water is added to dissolve the 2-ethyl-caproic acid salt. This solution separates into two layers which are separated further by ordinary methods. The lower water layer is acidified with sulfuric acid, and 2-ethyl-caproic acid is obtained. The yield is approximately the theoretical value. 2-ethylhexyl-2-ethylcaproic acid ester is obtained by the fractional distillation of the upper layer.

The hydrogen gas generated in the course of the reaction described above is highly pure and was approximately the theoretical value in volume. It can be used for hydrogenation of the raw material.

Examples of the process of the invention will be described herein below.

EXAMPLE 1

In a reactor (stainlss steel) provided with a reflux condenser, 78 g. of 2-ethyl-hexanol, 12 g. of sodium hydroxide and 2 g. of zinc oxide were charged and heated to the refluxing temperature (182°C.), of the alcohol and 2.5 ml. of water produced therein was distilled off. Hydrogen gas produced therein was released through a gasmeter into the atmosphere. In 90 minutes the generation of the hydrogen gas terminated (the amount of the gas generated was 0.6 mols), and the temperature of the reactor rose from the refluxing temperature to 230°C., at which point the reaction ended. The reaction system was allowed to cool off. The cooled reaction mixture was stirred and sodium salt of 2-ethyl-caproic acid formed therein was dissolved with water and the solution was left to stand and separated into the two layers, and the upper layer was subsequently fractionated by the ordinary method. By acidifying the lower water layer with sulfuric acid, 25.0 g. of 2-ethylcaproic acid was obtained by the fractional distillation of the upper layer. And 29.5 g. of 2-ethylhexyl-2-ethylcaproic acid ester were obtained.

EXAMPLE 2

In a reactor (nickel lined autoclave) provided with a reflux condenser, 92.8 g. of n-heptanol, 16.0 g. of sodium hydroxide and 3.5 g. of zinc carbonate were charged in the same manner as in Example 1. In 120 minutes, 4.2 ml. of water were distilled off and 0.86 mols of hydrogen were generated, and the reaction temperature rose from the refluxing temperature of the alcohol to 245°C. Subsequently, the reaction mixture was cooled to the room temperature and then treated by the same procedure of Example 1. Consequently, 39.8 g. of heptanoic acid from the lower water layer and 10.0 g. of heptylheptanoate ester from the upper layer were obtained.

EXAMPLE 3

Following the same procedure of Example 1, 102.0 g. of 2-ethylbutanol, 20.0 g. of sodium hydroxide and 4.4 g. of zinc chloride were charged to the reactor. In 540 minutes, 1.0 mol hydrogen was generated and the reaction temperature rose from the refluxing temperature of the alcohol to 210°C. The amount of the water produced throughout the entire course of the reaction was 4.0 ml. Thereafter, the reaction mixture was cooled to the room temperature and treated in the same manner as in the Example 1. Consequently, 28.0 g. of 2-ethylbutyric acid from the lower water layer and 43.6 g. of 2-ethylbutyl-2-ethylbutyrate ester from the upper layer were obtained.

EXAMPLE 4

Following the procedure of Example 1, 195 g. of 2-ethylhexanol, 42 g. of sodium hydroxide and 8.6 g. of zinc octoate were charged to the reactor. In 130 minutes, 1.7 mols of hydrogen were generated and the reaction temperature rose from the refluxing temperature of the alcohol to 220°C. The amount of the water produced throughout the entire course of the reaction was 8.6 ml. Thereafter, the reaction mixture was cooled to the normal room temperature and treated in the same manner as in Example 1. Consequently, 80 g. of 2-ethylcaproic acid from the lower water layer and 45 g. of 2-ethylhexyl-2-ethylcaproate ester from the upper layer were obtained.

When the same reaction mixture as obtained above was cooled to 150°C. and then treated in the same manner as in Example 1, 100 g. of 2-ethylcaproic acid from the lower layer and 10 g. of 2-ethylhexyl-2-etylcaproate ester from the upper layer were obtained.

EXAMPLE 5

When 174 g. of 2-ethylbutanol, 42 g. of sodium hydroxide and 2 g. of zinc powder were treated in the same manner as in Example 1, 1.9 mols of hydrogen were generated in 475 minutes, and the reaction temperature rose from the refluxing temperature of the alcohol to 210°C. The amount of the water produced throughout the entire course of the reaction was 10.2 ml. Thereafter, the reaction mixture was cooled to the normal room temperature and treated in the same manner as in Example 1. Consequently, 58 g. of 2-ethylbutyric acid from the lower water layer and 35 g. of 2-ethylbutyl-2-ethylbutyrate ester from the upper layer were obtained.

EXAMPLE 6

Following the procedure of Example 1, 216 g. of 2-methyloctanol, 42 g. of sodium hydroxide and 1.0 g. of zinc oxide were charged to the reactor. In 160 minutes, 1.5 mols of hydrogen were generated and the reaction temperature rose to 252°C. The amount of the water produced was 8.0 ml. The reaction mixture was treated in the same manner as in Example 1. Consequently, 87 g. of 2-methyloctoic acid and 52 g. of 2-methyloctyl-2-methyloctoate ester were obtained.

EXAMPLE 7

When 237 g. of decylalcohol, 42 g. of sodium hydroxide and 0.5 g. of zinc powder were treated in the same manner as in Example 1, 1.8 mols of hydrogen were generated in 185 minutes, and the reaction temperature rose to 260°C. The amount of the water distilled out was 9.0 ml. Consequently, 113 g. of decanoic acid and 21 g. of decyldecanoate ester were obtained.

The fatty acid salts are readily converted into the corresponding acids by the action of aqueous mineral acids (as can be seen from the foregoing examples). The salts and their corresponding acids and esters are commercially important precursors for other compounds containing long, straight-chain units. The fatty acid salts and esters, therefore, are useful in the production of inks, solvents, defoaming agents, cosmetic materials and the like.

What is claimed is:

1. A process for producing a fatty acid salt and ester thereof comprising reacting a primary aliphatic alcohol having from 6 to 18 carbon atoms with an hydroxide of an alkali metal at atmospheric pressure in the presence of a catalytic amount of metallic zinc or a zinc compound by refluxing the primary aliphatic alcohol and simultaneously distilling off water and removing hydrogen gas evolved during the reaction.

2. The process of claim 1 wherein said primary aliphatic alcohol has from 6 to 10 carbon atoms.

3. The process of claim 1 wherein said zinc compound is zinc oxide, zinc chloride, zinc carbonate or zinc 2-ethylhexaoate.

4. The process of claim 1 wherein the amount of caustic alkali is from 50 to 90 mol percent based on the weight of the primary aliphatic alcohol.

5. The process of claim 1 wherein said caustic alkali is sodium hydroxide.

6. The process of claim 5 wherein the sodium hydroxide is in the flake form.

7. The process of claim 1 wherein the primary aliphatic alcohol is 2-ethyl-hexanol.

8. The process of claim 1 wherein the zinc compound is zinc oxide present in a catalytic amount.

* * * * *